US00PP32328P2

(12) United States Plant Patent
Koppe

(10) Patent No.: US PP32,328 P2
(45) Date of Patent: Oct. 13, 2020

(54) ***BEGONIA* PLANT NAMED 'KRSWEWH01'**

(50) Latin Name: ***Begonia* x *hiemalis***
Varietal Denomination: KRSWEWH01

(71) Applicant: Lubbertus H. Koppe, Putten (NL)

(72) Inventor: Lubbertus H. Koppe, Putten (NL)

(73) Assignee: KOPPE ROYALTY B.V., Putten (NL)

( * ) Notice: Subject to any disclaimer, the term of this patent is extended or adjusted under 35 U.S.C. 154(b) by 0 days.

(21) Appl. No.: 16/602,493

(22) Filed: Oct. 17, 2019

(51) Int. Cl.
*A01H 5/02* (2018.01)
*A01H 6/18* (2018.01)

(52) U.S. Cl.
USPC ..... Plt./345

(58) Field of Classification Search
USPC ..... Plt./345
See application file for complete search history.

*Primary Examiner* — Annette H Para
(74) *Attorney, Agent, or Firm* — C. A. Whealy

(57) ABSTRACT

A new and distinct cultivar of *Begonia* plant named 'KRSWEWH01' characterized by its compact, broadly upright and mounded plant habit; moderately vigorous growth habit; moderately freely branching habit; dark green to greyed green-colored leaves; freely flowering habit; double-type male flowers that are white in color and held above and beyond the foliar plane; and good postproduction longevity.

2 Drawing Sheets

Figure 1:
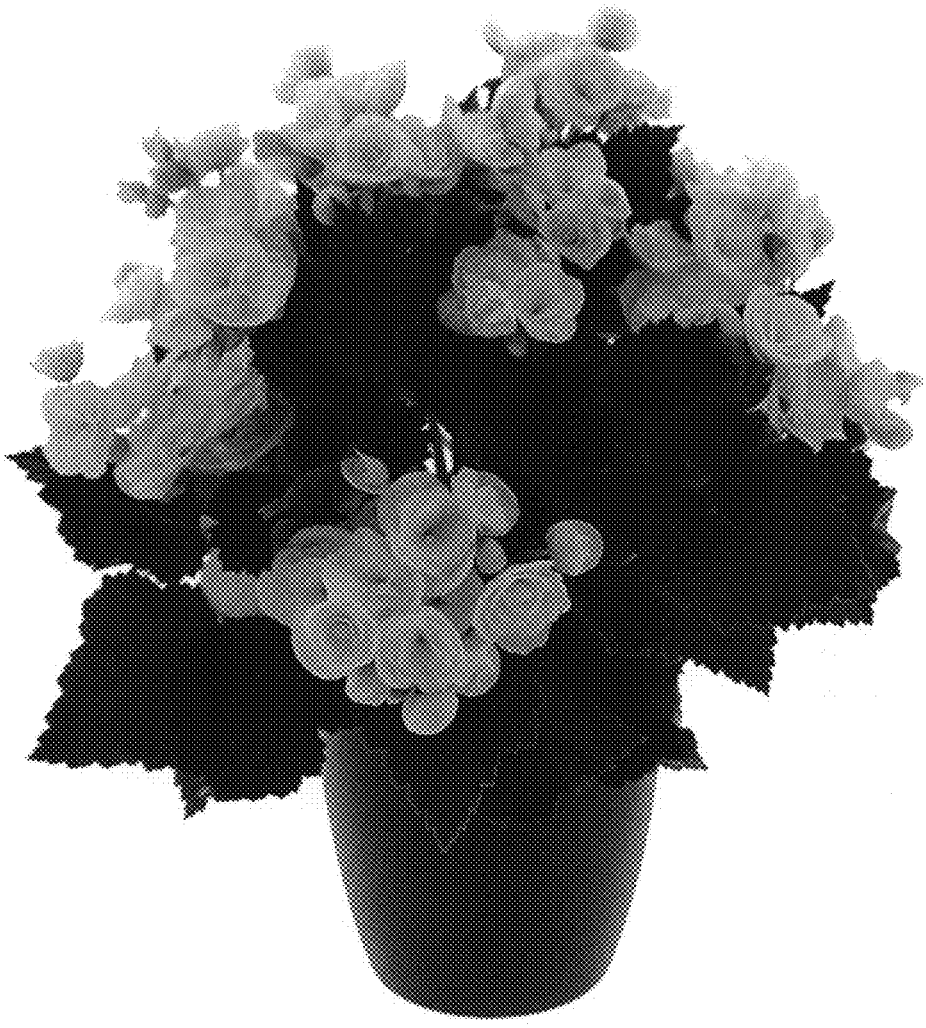

Botanical designation: *Begonia* x *hiemalis*.
Cultivar denomination: 'KRSWEWH01'.

BACKGROUND OF THE INVENTION

The present invention relates to a new and distinct cultivar of *Begonia* plant, botanically known as *Begonia* x *hiemalis*, commercially referred to as an Elatior *Begonia* and hereinafter referred to by the name 'KRSWEWH01'.

The new *Begonia* plant is a product of a planned breeding program conducted by the Inventor in Ermelo, The Netherlands. The objective of the breeding program is to create new freely-branching *Begonia* plants with excellent postproduction longevity and attractive flower color.

The new *Begonia* plant is a naturally-occurring whole plant mutation of a proprietary selection of *Begonia* x *hiemalis* identified as code number KV08-1348-007, not patented. The new *Begonia* plant was discovered and selected by the Inventor as a single flowering plant from within a population of plants of the parent selection in a controlled greenhouse environment in Ermelo, The Netherlands in March, 2015.

Asexual reproduction of the new *Begonia* plant by terminal vegetative cuttings taken in a controlled greenhouse environment in Ermelo, The Netherlands since February, 2016 has shown that the unique features of this new *Begonia* plant are stable and reproduced true to type in successive generations.

SUMMARY OF THE INVENTION

Plants of the new *Begonia* have not been observed under all possible combinations of environmental conditions and cultural practices. The phenotype may vary somewhat with variations in environmental conditions such as temperature, daylength and light intensity, without, however, any variance in genotype.

The following traits have been repeatedly observed and are determined to be the unique characteristics of 'KRSWEWH01'. These characteristics in combination distinguish 'KRSWEWH01' as a new and distinct *Begonia* plant:

1. Compact, broadly upright and mounded plant habit.
2. Moderately vigorous growth habit.
3. Moderately freely branching habit.
4. Dark green to greyed green-colored leaves.
5. Freely flowering habit.
6. Double-type male flowers that are white in color and held above and beyond the foliar plane.
7. Good postproduction longevity.

Plants of the new *Begonia* differ primarily from plants of the mutation parent selection in flower color as plants of the new *Begonia* have white-colored flowers whereas plants of the mutation parent selection have pink-colored flowers.

Plants of the new *Begonia* can be compared to plants of *Begonia* x *hiemalis* 'White Netja', not patented. In side-by-side comparisons conducted in Ermelo, The Netherlands, plants of the new *Begonia* differ primarily from plants of 'White Netja' in the following characteristics:

1. Plants of the new *Begonia* are more compact than plants of 'White Netja'.
2. Plants of the new *Begonia* have smaller flowers than plants of 'White Netja'.
3. Plants of the new *Begonia* have double-type flowers whereas than plants of 'White Netja' have semi double-type flowers.

BRIEF DESCRIPTION OF THE PHOTOGRAPHS

The accompanying colored photographs illustrate the overall appearance of the new *Begonia* plant showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet (FIG. 1 of 2) comprises a side perspective view of a typical plant of 'KRSWEWH01' grown in a container.

Figure 2:
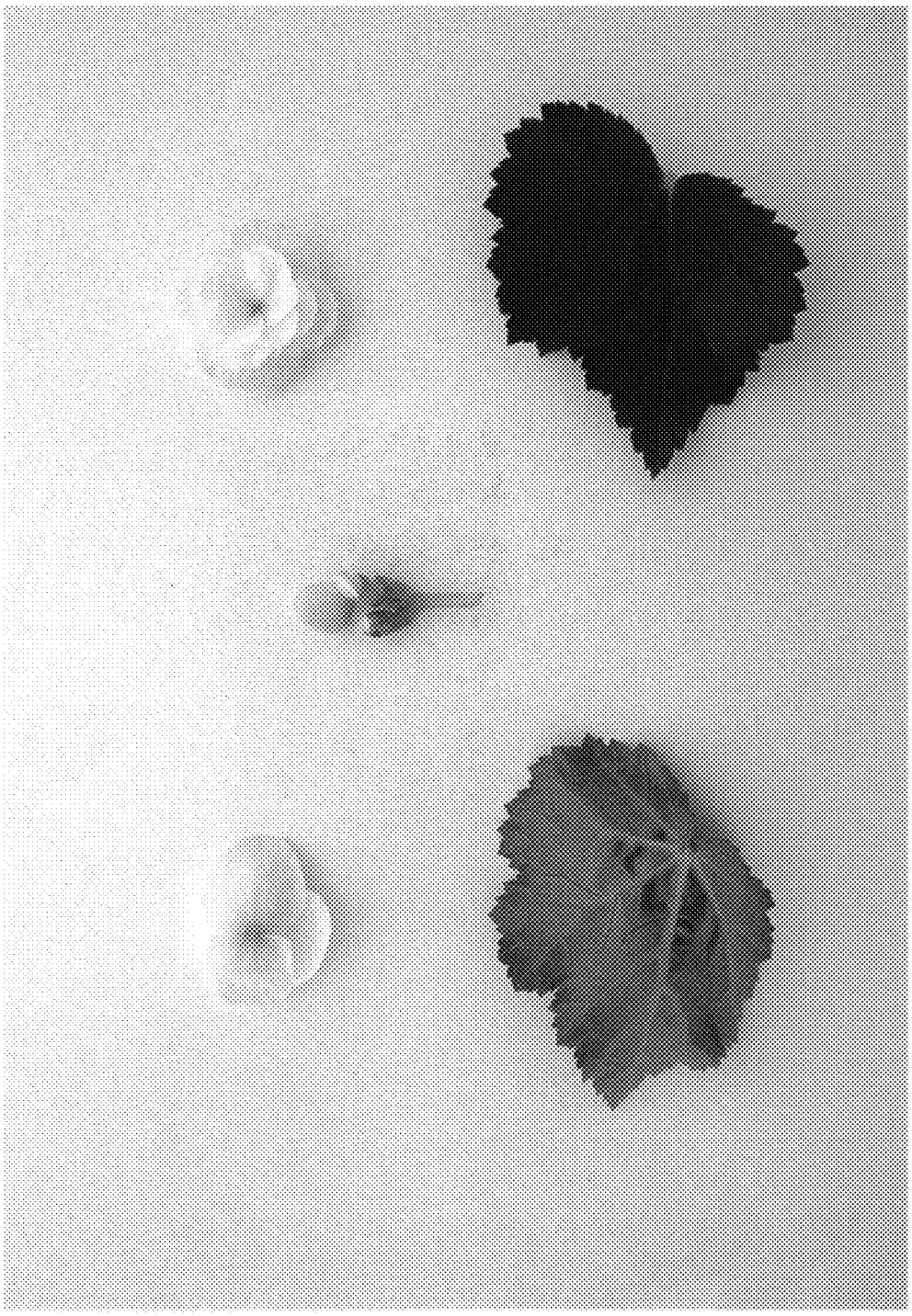

The photograph on the second sheet (FIG. 2 of 2) are close up views of the upper (right) and lower (left) surfaces of typical leaves and flowers of 'KRSWEWH01', and in the center of the photograph is a close-up view of typical flower buds.

DETAILED BOTANICAL DESCRIPTION

The aforementioned photographs and following observations and measurements describe plants grown during the late spring and early summer in 10.5-cm containers in a glass-covered greenhouse in Ermelo, The Netherlands and under cultural practices typical of commercial *Begonia* production. During the production of the plants, day temperatures ranged from 20° C. to 22° C. and night temperatures ranged from 16° C. to 18° C. Plants were three months old when the photographs and description were taken. In the following description, color references are made to The Royal Horticultural Society Colour Chart, 2015 Edition, except where general terms of ordinary dictionary significance are used.

Botanical classification: *Begonia* x *hiemalis* 'KRSWEWH01'.

Parentage: Naturally-occurring whole plant mutation of a proprietary selection of *Begonia* x *hiemalis* identified as code number KV08-1348-007, not patented.

Propagation:

*Type*.—By terminal vegetative cuttings.

*Time to initiate roots, summer and winter*.—About 20 days at temperatures about 20° C.

*Time to produce a rooted young plant, summer and winter*.—About five weeks at temperatures about 20° C.

*Root description*.—Fine, fibrous; typically white to orange brown in color, actual color of the roots is dependent on substrate composition, water quality, fertilizer type and formulation, substrate temperature and physiological age of roots.

*Rooting habit*.—Freely branching; medium density; plants of the new *Begonia* have not been observed to form tubers.

Plant description:

*Plant habit and form*.—Broadly upright and mounded plant habit; overall plant shape, globular.

*Growth habit*.—Moderately vigorous growth habit and moderate growth rate; suitable for 9-cm and larger containers; under optimal environmental and cultural conditions, usually about eleven weeks from rooted cuttings are required to produce proportional plants in 10.5-cm containers.

*Branching habit*.—Moderately freely branching with about three primary branches each with about three secondary branches developing per plant.

*Plant height, soil level to top of foliar plane*.—About 22 cm.

*Plant height, soil level to top of floral plane*.—About 24.3 cm.

*Plant width*.—About 31.8 cm.

*Lateral branches*.—Length: About 11.5 cm. Diameter: About 7 mm. Internode length: About 2.2 cm. Strength: Moderately strong. Aspect: Erect to about 60° from vertical. Texture and luster: Sparsely pubescent; slightly glossy. Color, developing and developed: Close to 146B. Lenticels: None observed on plants of the new *Begonia* to date.

*Leaves*.—Arrangement: Alternate, simple. Length: About 11.1 cm. Width: About 9.9 cm. Shape: Broadly ovate to unequal reniform. Apex: Short apiculate. Base: Obliquely cordate, lobes free. Margin: Crenate to serrate; moderately undulate. Texture and luster, upper surface: Smooth, glabrous; moderately velvety; slightly to moderately glossy. Texture and luster, lower surface: Smooth, glabrous; slightly velvety; very slightly to slightly glossy. Venation pattern: Laciniate, pinnate. Color: Developing leaves, upper surface: Slightly darker than 147A. Developing leaves, lower surface: Close to 176B to 176C. Fully expanded leaves, upper surface: Darker than between 147A and N189A; venation, close to 143A. Fully expanded leaves, lower surface: Close to 148A, slightly to moderately tinged with close to 182A; venation, close to 146B to 146C. Petioles: Length: About 4.4 cm. Diameter: About 5 mm. Strength: Low, flexible. Texture and luster, upper and lower surfaces: Sparsely pubescent; slightly glossy. Color, upper surface: Close to between N148B and 152B variably tinged with close to 180A. Color, lower surface: Close to 152B. Stipules: Quantity and appearance: Two leafy stipules at the base of each leaf. Length: About 9 mm. Width: About 1 cm. Shape: Broadly ovate. Apex: Obtuse. Base: Broadly cuneate. Margin: Ciliate. Color, upper and lower surfaces: Close to 146D.

Flower description:

*Flower form and flowering habit*.—Double-type male rotate flowers arranged in axillary cymes; to date, female flower development has not been observed on plants of the new *Begonia*; typically about nine flowers per cyme, numerous cymes in flower simultaneously and about 250 flowers developing per plant; flowers face upright to outwardly and are positioned above and beyond the foliar plane.

*Natural flowering season*.—Plants flower continuously from the spring into the autumn in The Netherlands.

*Flower longevity*.—Individual flowers last about ten days on the plant; flowers not persistent.

*Fragrance*.—None detected.

*Inflorescence height*.—About 13.7 cm.

*Inflorescence diameter*.—About 7.4 cm.

*Flower buds*.—Length: About 1.6 cm. Diameter: Ranging from about 0.9 cm to 1.6 cm. Shape: Broadly obovate to nearly circular, flattened. Texture and luster: Smooth, glabrous; moderately velvety; matte. Color: Close to 157A to 157B; towards the base, close to 145B.

*Male flowers*.—Diameter: About 4.5 cm. Depth: About 1.7 cm. Tepals: Quantity and arrangement: About four arranged in two whorls. Length, inner whorl: About 2.2 cm. Length, outer whorl: About 2.6 cm. Width, inner whorl: About 2.6 cm. Width, outer whorl: About 2.7 cm. Shape: Reniform. Apex: Obtuse to rounded. Base: Broadly cuneate. Margin: Entire, not undulate. Texture and luster, upper surface: Smooth, glabrous; velvety; matte. Texture and luster, lower surface: Smooth, glabrous; moderately velvety; moderately glossy. Color, inner whorl: When opening, upper surface: Close to NN155B.

When opening, lower surface: Close to NN155B; towards the base, close to 155C. Fully opened, upper and lower surfaces: Close to NN155D; towards the base, close to 1B; venation, similar to lamina color; color does not change with development. Color, outer whorl: When opening, upper surface: Close to 155C. When opening, lower surface: Close to 157D; towards the base, close to 157A. Fully opened, upper surface: Close to 157D; towards the base and apex, close to 157A; venation, similar to lamina color; color does not change with development. Fully opened, lower surface: Close to 157A; towards the base, close to 145C; venation, similar to lamina color; with development, color in the center becomes tinged with close to 181D. Tepaloids: Quantity and arrangement per flower: Typically about 16 per flower arranged in about four whorls. Length: About 0.9 cm to 1.8 cm. Width: About 0.6 cm to 2.3 cm. Shape: Broadly obovate to obovate. Apex: Obtuse to rounded. Base: Cuneate to broadly cuneate. Margin: Entire; not undulate. Texture and luster, upper surface: Smooth, glabrous; velvety; matte. Texture and luster, lower surface: Smooth, glabrous; moderately velvety; matte. Color: When opening, upper surface: Close to NN155B; towards the base, close to 155C. When opening, lower surface: Close to NN155D; towards the base, close to 1B. Fully opened, upper surface: Close to NN155D; towards the base, close to 1B; venation, similar to lamina color; color does not change with development. Fully opened, lower surface: Close to NN155D; towards the base, close to 1B; venation, close to NN155B and proximally, close to 155C; color does not change with development.

*Flower bracts*.—Quantity and arrangement: Two positioned at the top of the peduncle. Length: About 1.3 cm. Width: About 1.4 cm. Shape: Reniform. Apex: Obtuse to broadly and bluntly acute. Base: Broadly cuneate. Margin: Finely ciliate. Color, upper and lower surfaces: Close to 144B.

*Peduncles*.—Length: About 11.7 cm. Diameter: About 3.5 mm. Strength: Moderately strong. Aspect: About 35° from lateral branch axis. Texture and luster: Moderately pubescent; moderately glossy. Color: Close to 146D.

*Pedicels*.—Length: About 3.2 cm. Diameter: About 2.5 mm. Strength: Moderately strong. Aspect: About 20° from peduncle axis. Texture and luster: Moderately pubescent; moderately glossy. Color, upper surface: Close to 144B, occasionally slightly tinged with close to 165B. Color, lower surface: Close to 144C and 145A.

*Reproductive organs*.—Stamens (present on male flowers only): No stamens observed as all stamens transformed into tepaloids. Pistils (present on female flowers only): To date, no female flower development has been observed on plants of the new *Begonia*. Seeds and fruits: To date, seed and fruit development have not been observed on plants of the new *Begonia*.

Pathogen & pest resistance: To date, resistance to pathogens and pests common to *Begonia* plants has not been observed on plants of the new *Begonia*.

Temperature tolerance: Plants of the new *Begonia* have been observed to tolerate high temperatures about 35° C. and to be suitable for USDA Hardiness Zones 10 to 12.

It is claimed:

1. A new and distinct *Begonia* plant named 'KRSWEWH01' as illustrated and described.

* * * * *